(12) United States Patent
Quinn et al.

(10) Patent No.: US 9,468,530 B2
(45) Date of Patent: Oct. 18, 2016

(54) METHODS OF IMPLANTING ORTHOPEDIC DEVICES

(71) Applicant: Smith & Nephew, Inc., Cordova, TN (US)

(72) Inventors: Nathaniel Quinn, Arlington, TN (US); Jeffrey Joel Shea, Memphis, TN (US)

(73) Assignee: Smith & Nephew, Inc., Cordova, TN (US)

( * ) Notice: Subject to any disclaimer, the term of this patent is extended or adjusted under 35 U.S.C. 154(b) by 0 days.

(21) Appl. No.: 14/616,525

(22) Filed: Feb. 6, 2015

(65) Prior Publication Data

US 2015/0150686 A1 Jun. 4, 2015

Related U.S. Application Data

(62) Division of application No. 13/156,248, filed on Jun. 8, 2011, now Pat. No. 8,979,926.

(60) Provisional application No. 61/466,817, filed on Mar. 23, 2011, provisional application No. 61/422,903, filed on Dec. 14, 2010, provisional application No. 61/352,705, filed on Jun. 8, 2010, provisional application No. 61/352,722, filed on Jun. 8, 2010.

(51) Int. Cl.
*A61F 2/34* (2006.01)
*A61B 17/80* (2006.01)
(Continued)

(52) U.S. Cl.
CPC ............ *A61F 2/34* (2013.01); *A61B 17/8066* (2013.01); *A61F 2/30734* (2013.01); *A61F 2/30771* (2013.01); *G06F 9/45533* (2013.01); *A61B 17/82* (2013.01); *A61B 17/866* (2013.01); *A61B 17/8685* (2013.01); *A61F 2/30749* (2013.01); *A61F 2/30907* (2013.01); *A61F 2/30965* (2013.01); *A61F 2002/30011* (2013.01); *A61F 2002/3038* (2013.01);
(Continued)

(58) Field of Classification Search
CPC ................. A61F 2/30734; A61F 2002/30169; A61F 2002/30189; A61F 2002/30736
See application file for complete search history.

(56) References Cited

U.S. PATENT DOCUMENTS

| 4,274,163 A * | 6/1981 | Malcom et al. ... A61B 17/8808 606/94 |
| 5,176,711 A | 1/1993 | Grimes |

(Continued)

OTHER PUBLICATIONS

International Search Report and Written Opinion of the International Searching Authority of Application No. PCT/US2011/039660 mailed Feb. 17, 2012.

*Primary Examiner* — Marcia Watkins
(74) *Attorney, Agent, or Firm* — Taft Stettinius & Hollister LLP

(57) ABSTRACT

Systems, devices, and methods are provided for orthopedic implants. The implants may include a base member, such as an acetabular shell or an augment, that is configured to couple with an augment, flange cup, mounting member, or any other suitable orthopedic attachment. An implant may include abuse member that has at least two projections with a gap between the projections. The gap between the projections allows the implant to be implanted around another implanted component, such as around a bone screw of an acetabular shell. The implant may include a fixation element, such as a screw or a cement trough, on one or more projections to couple the implant to an implanted acetabular shell. The implant may also include timing marks to facilitate alignment with corresponding marks on another implanted component.

13 Claims, 3 Drawing Sheets

(51) Int. Cl.
*G06F 9/455* (2006.01)
*A61F 2/30* (2006.01)
*A61B 17/82* (2006.01)
*A61B 17/86* (2006.01)
*A61F 2/46* (2006.01)

(52) U.S. Cl.
CPC .......... *A61F 2002/3082* (2013.01); *A61F 2002/3092* (2013.01); *A61F 2002/3096* (2013.01); *A61F 2002/30169* (2013.01); *A61F 2002/30189* (2013.01); *A61F 2002/30326* (2013.01); *A61F 2002/30387* (2013.01); *A61F 2002/30449* (2013.01); *A61F 2002/30462* (2013.01); *A61F 2002/30471* (2013.01); *A61F 2002/30474* (2013.01); *A61F 2002/30507* (2013.01); *A61F 2002/30538* (2013.01); *A61F 2002/30578* (2013.01); *A61F 2002/30579* (2013.01); *A61F 2002/30611* (2013.01); *A61F 2002/30617* (2013.01); *A61F 2002/30736* (2013.01); *A61F 2002/30841* (2013.01); *A61F 2002/348* (2013.01); *A61F 2002/3412* (2013.01); *A61F 2002/3429* (2013.01); *A61F 2002/3441* (2013.01); *A61F 2002/3448* (2013.01); *A61F 2002/3487* (2013.01); *A61F 2002/4615* (2013.01); *A61F 2002/4619* (2013.01)

(56) References Cited

U.S. PATENT DOCUMENTS

| | | |
|---|---|---|
| 5,326,368 A | 7/1994 | Collazo |
| 5,425,778 A | 6/1995 | Zichner et al. |
| 5,458,637 A | 10/1995 | Hayes |
| 5,531,793 A | 7/1996 | Kelman et al. |
| 5,549,685 A | 8/1996 | Hayes |
| 5,658,338 A | 8/1997 | Tullos et al. |
| 5,658,347 A | 8/1997 | Sarkisian et al. |
| 5,725,587 A | 3/1998 | Garber |
| 6,162,257 A | 12/2000 | Gustilo et al. |
| 6,280,476 B1 | 8/2001 | Metzger et al. |
| 6,416,553 B1 | 7/2002 | White et al. |
| 6,458,161 B1 | 10/2002 | Gibbs et al. |
| 6,488,713 B1 | 12/2002 | Hershberger |
| 6,500,208 B1 | 12/2002 | Metzger et al. |
| 6,908,486 B2 | 6/2005 | Lewallen |
| 6,916,340 B2 | 7/2005 | Metzger et al. |
| 7,044,974 B2 | 5/2006 | Garber et al. |
| 7,179,298 B2 | 2/2007 | Greenlee |
| 7,291,177 B2 | 11/2007 | Gibbs |
| 7,547,327 B2 | 6/2009 | Collazo |
| 7,621,962 B2 | 11/2009 | Lakin |
| 7,635,447 B2 | 12/2009 | Hamman et al. |
| 7,651,501 B2 | 1/2010 | Penenberg et al. |
| 7,713,306 B2 | 5/2010 | Gibbs |
| 7,766,969 B2 | 8/2010 | Justin et al. |
| 7,780,739 B2 | 8/2010 | Lakin et al. |
| 7,922,769 B2 | 4/2011 | Deffenbaugh et al. |
| 7,923,020 B2 | 4/2011 | King et al. |
| 2001/0037156 A1 | 11/2001 | Burstein et al. |
| 2002/0042654 A1 | 4/2002 | Masini |
| 2004/0024340 A1 | 2/2004 | Schwenn et al. |
| 2004/0049284 A1* | 3/2004 | German ............ A61F 2/30734 623/20.15 |
| 2004/0162619 A1* | 8/2004 | Blaylock ........... A61B 17/1764 623/20.16 |
| 2004/0199258 A1 | 10/2004 | Macara |
| 2004/0225369 A1 | 11/2004 | Lakin et al. |
| 2005/0021148 A1 | 1/2005 | Gibbs |
| 2005/0240276 A1 | 10/2005 | Shea et al. |
| 2005/0246027 A1 | 11/2005 | Metzger et al. |
| 2006/0241776 A1 | 10/2006 | Brown et al. |
| 2007/0129809 A1 | 6/2007 | Meridew et al. |
| 2007/0142922 A1 | 6/2007 | Lewis et al. |
| 2007/0179627 A1* | 8/2007 | Gustilo ............. A61F 2/30734 623/20.15 |
| 2007/0179629 A1 | 8/2007 | Murphy |
| 2007/0198022 A1 | 8/2007 | Lang et al. |
| 2008/0021568 A1 | 1/2008 | Tulkis et al. |
| 2009/0088865 A1 | 4/2009 | Brehm |
| 2009/0149964 A1* | 6/2009 | May ................. A61B 17/155 623/20.15 |
| 2009/0204225 A1 | 8/2009 | Meridew et al. |
| 2009/0240256 A1 | 9/2009 | Smith |
| 2009/0326660 A1 | 12/2009 | Abendschein |
| 2009/0326670 A1 | 12/2009 | Keefer et al. |
| 2010/0030339 A1 | 2/2010 | Berelsman et al. |
| 2010/0145466 A1 | 6/2010 | Slone |
| 2010/0312349 A1 | 12/2010 | Berelsman et al. |
| 2011/0009973 A1 | 1/2011 | Meyers et al. |
| 2011/0009975 A1 | 1/2011 | Allen et al. |
| 2011/0054628 A1 | 3/2011 | Banks et al. |
| 2011/0093086 A1 | 4/2011 | Witt et al. |

* cited by examiner

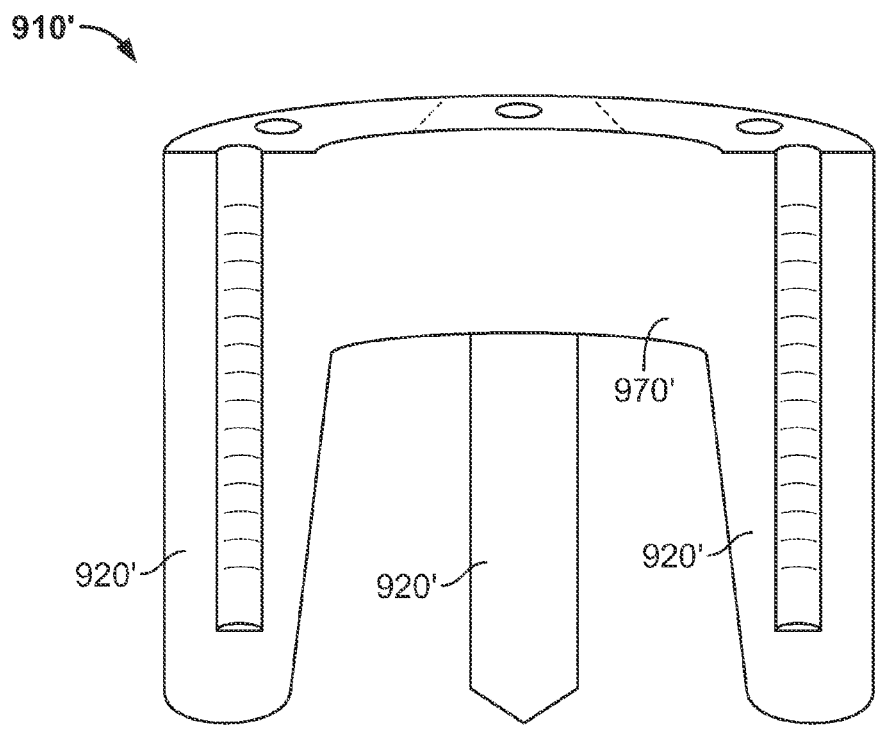
FIG. 8
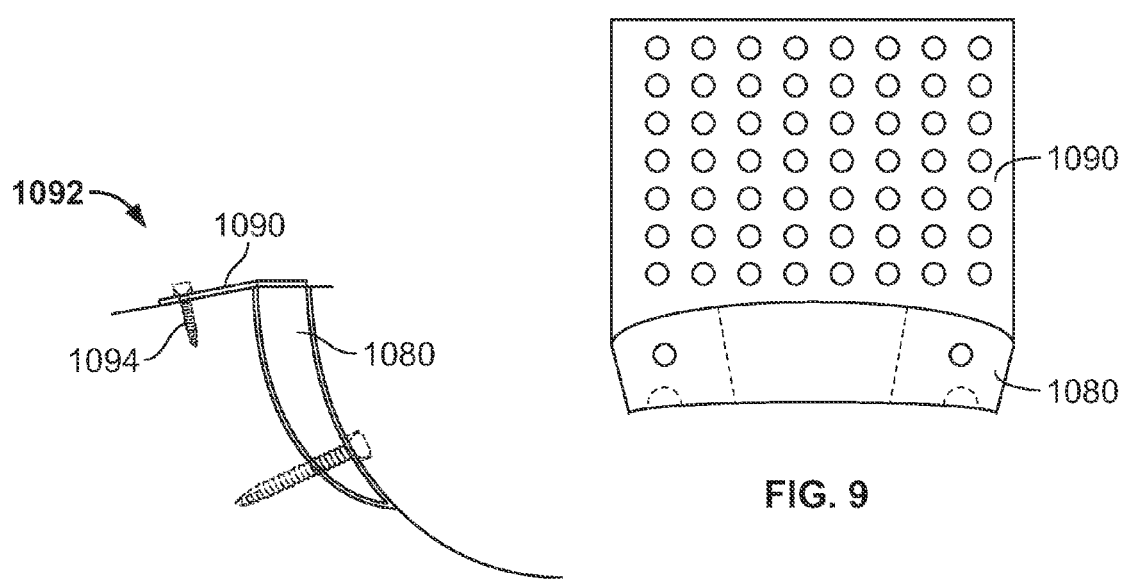
FIG. 10
FIG. 9

METHODS OF IMPLANTING ORTHOPEDIC DEVICES

CROSS-REFERENCE TO RELATED APPLICATIONS

This application is a division of U.S. patent application Ser. No. 13/156,248, filed Jun. 8, 2011, now U.S. Pat. No. 8,979,926, which claims the benefit of U.S. Provisional Patent Application No. 61/352,705, filed Jun. 8, 2010, U.S. Provisional Application No. 61/352,722, filed Jun. 8, 2010, U.S. Provisional Application No. 61/422,903, filed Dec. 14, 2010, and U.S. Provisional Application No. 61/466,817, filed Mar. 23, 2011, which are hereby incorporated by reference herein in their entireties.

BACKGROUND

Joints often undergo degenerative changes due to a variety of reasons. When joint degeneration becomes advanced or irreversible, it may become necessary to replace the natural joint with a prosthetic joint. Artificial implants, including hip joints, shoulder joints, and knee joints are widely used in orthopedic surgery. Specifically, hip joint prostheses are common. The human hip joint acts mechanically as a ball and socket joint, wherein the ball-shaped head of the femur is positioned within the socket-shaped acetabulum of the pelvis. Various degenerative diseases and injuries may require replacement of all or a portion of a hip using synthetic materials, typically metals, ceramics, or plastics.

More particularly, natural hips often undergo degenerative changes, requiring replacement of the hip joint with a prosthetic joint. Often, the hip is replaced with two bearing surfaces between the femoral head and the acetabutum. The first bearing surface is typically a prosthesis shell or acetabular cup, which may be formed of metal, ceramic material, or as otherwise desired. A liner (conventionally formed of polyethylene material such as ultra high molecular weight polyethylene, a ceramic material, or in some cases, even a metal liner) is then fit tightly within the shell to provide an inner bearing surface that receives and cooperates with an artificial femoral head in an articulating relationship to track and accommodate the relative movement between the femur and the acetabulum.

The cup (or a cup and liner assembly) is typically fixed either by placing screws through apertures in the cup or by securing the cup with cement. In some cases, only a liner is cemented in a patient due to poor bone stock. In other cases, a cup having a porous surface may be press fit into the reamed acetabular surface.

It may become necessary to conduct a second or subsequent surgery in order to replace a prosthetic joint with a (often larger) replacement joint. Such surgeries often become necessary due to further degeneration of bone or advancement of a degenerative disease, requiring removal of further bone and replacement of the removed, diseased bone with a larger or enhanced prosthetic joint, often referred to as a revision prosthesis. For example, bone is often lost around the rim of the acetabulum, and this may provide less rim coverage to securely place a press-fit cup. Such surgeries may thus be referred to as revision surgeries.

In acetabular revision surgery, an acetabular prosthesis generally includes additional mounting elements, such as augments, flanges, hooks, plates, or any other attachment or mounting points or members that provide additional support and/or stability for the replacement prosthesis once positioned. These additional mounting or attachment members are often required due to bone degeneration, bone loss, or bone defects in the affected area (in this instance, the hip joint).

Various types of these mounting members (which term is intended to include but not be limited to flanges, blades, plates and/or hooks) may be provided in conjunction with a prosthesis system in order to help the surgeon achieve optimal fixation, non-limiting examples of which include iliac flanges (providing securement and fixation in and against the ilium region of the pelvis), ischial blades (providing securement and fixation in and against the ischium), and obturator hooks (providing securement and inferior fixation by engaging the obturator foramen). Although there have been attempts to provide such mounting attachments with modularity, the solutions to date have generally fallen short of providing true modularity. Instead, they typically provide a few discrete positions at which the mounting members may be positioned, without providing the surgeon a fuller range of decision options.

Additionally, in some primary surgeries and more often in revision surgeries, the acetabulum may have a bone defect or void that the surgeon must fill with bone grafts before inserting a new shell. This can be time consuming and expensive, and may subject the patient to additional health risks. Some techniques use an augment in connection with the acetabular shell, which can be coupled to or otherwise attached to the outer surface of the shell.

With current augments, the surgeon can attach the augment to the bone and then implant the cup. However, many acetabular shells rely on bone screws to achieve proper fixation and the augment often gets in the way of a screw. In short, surgeons need the freedom to place screws in the best location, but this compromises their ability to use augments. With current systems, it also takes an increased amount of time surgical time to trial the component orientation and then try to find good bone fixation for the cup. The surgeon will often have to free-hand the amount of bone removed while estimating the size of augment needed. In the cases where bone is often deficient, surgeons are hesitant to take away any more bone than necessary.

Various additional features and improved features intended for use and application with various types of joint implants are also described herein, such as improved bone screws, improved coatings, and various augment removal and insertion options.

SUMMARY

Disclosed herein are systems, devices, and methods for providing modular orthopedic implants. The implants may include a base member, such as an acetabular shell or an augment, that is configured to couple with an augment, flange cup, mounting member, any other suitable orthopedic attachment, or any combinations thereof. Mounting members include, for example, flanges, blades, hooks, and plates. In some embodiments, the orthopedic attachments may be adjustably positionable about the base member or other attachments thereby providing modularity for assembling and implanting the device. Various securing and/or locking mechanisms may be used between the components of the implant. In certain embodiments, the orthopedic attachments are removably coupled to the base member or other components. In certain embodiments, the orthopedic attachments are integrally provided on the base member or other components, yet may still be adjustably positionable thereabout. In some embodiments, expandable augments, base members, or other bone filling devices are provided. In some embodiments, surface features are provided that create friction and allow for surrounding bone ingrowth at the interface of the implants and a patient's bone.

Systems, devices, and methods described herein provide implants having a plurality of projections and optional fixation elements. In certain embodiments, an orthopedic augment includes a base member to which at least two projections are coupled, the at least two projections having a gap therebetween, and a fixation element provided on one or more of the at least two projections. The fixation element may be a cement trough. In certain embodiments, the base member is shaped to couple with an implant. For example, a first surface of the base member that contacts the implant may be substantially arcuate. The at least two projections may be disposed in substantially the same direction. The length of the at least two projections may be substantially the same, or the length of one of the at least two projections may be different than the respective length of another of the at least two projections. In some embodiments, the base member includes one or more fixation elements such as screw holes configured to receive a fastener. In some embodiments, the base member includes a connection element configured to receive a driver handle for placing the orthopedic augment into a patient's joint. In some embodiments, the base member includes timing marks configured to align with corresponding timing marks on an implant. In some embodiments, the augment may further include flanges, blades, plates, or hooks attached thereto.

In certain embodiments, a method of implanting an orthopedic device in a patient's joint may include placing an implant within the patient's joint, the implant secured to the joint via a fixation device, preparing a space in the patient's bone proximate the implant and the fixation device, providing an augment that includes at least two projections having a gap therebetween, and inserting the augment into the prepared space by positioning the augment around the fixation member such that the fixation member extends through the gap between the at least two projections of the augment. The method may further include forming a cement trough on one or more of the at least two projections, and setting the augment by pouring cement into the cement trough. In some embodiments, the method includes setting the augment using screws. The preparing may include rasping or reaming the patient's bone with a broach. The broach may have approximately the same cross-sectional profile as the augment. In some embodiments, the amount of bone removed may be limited by using a depth stop disposed on the broach. The inserting may include attaching the augment to a driver handle for positioning the augment into the prepared space. The method may further include aligning timing marks disposed on the augment with timing marks disposed on the implant. In some embodiments, the augment further comprises flanges, blades, plates, or hooks attached thereto. In some embodiments, the placing including mounting an acetabular shell or cage within the patient's acetabulum.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which:

FIG. 8 shows a front perspective view of an illustrative augment having three projections;

FIG. 9 shows a top plan view of an augment having an illustrative flange; and

FIG. 10 shows a partial cross-section elevation view of an illustrative augment with a flange installed in an acetabulum.

DETAILED DESCRIPTION

To provide an overall understanding of the systems, devices, and methods described herein, certain illustrative embodiments will be described. Although the embodiments and features described herein are specifically described for use in connection with acetabular systems, it will be understood that all the components, connection mechanisms, adjustable systems, fixation methods, manufacturing methods, coatings, and other features outlined below may be combined with one another in any suitable manner and may be adapted and applied to medical devices and implants to be used in other surgical procedures, including, but not limited to: spine arthroplasty, cranio-maxiliofaciat surgical procedures, knee arthroplasty, shoulder arthroplasty, as well as foot, ankle, hand, and other extremity procedures.

Various implants and other devices described herein in their various embodiments may be used in conjunction with any appropriate reinforcement material, non-limiting examples of which include bone cement, appropriate polymers, resorbable polyurethane, and/or any materials provided by PolyNovo Blomaterials Limited, or any suitable combinations thereof. Further non-limiting examples of potential materials that may be used are described in the following references: U.S. Patent Application Publication No. 2006/0051394, entitled "Biodegradable Polyurethane and Polyurethane Ureas," U.S. Patent Application Publication No. 2005/0197422, entitled "Biocompatibie Polymer Compositions for Dual or Multi Staged Curing," U.S. Patent Application Publication No. 2005/0238683, entitled "Biodegradable PolyurethaneUrea Compositions," U.S. Patent Application Publication No. 2007/0225387, entitled "Polymer Compositions for Dual or Multi Staged Curing," U.S. Patent Application Publication No. 2009/0324675, entitled "Biocompatible Polymer Compositions," U.S. Patent Application Publication No. 2009/0175921, entitled "Chain Extenders," and U.S. Patent Application Publication No. 2009/0099600, entitled "High Modulus Polyurethane and Polyurethane/Urea Compositions." Each of the prior references is incorporated by reference herein in its entirety.

Figure 1:
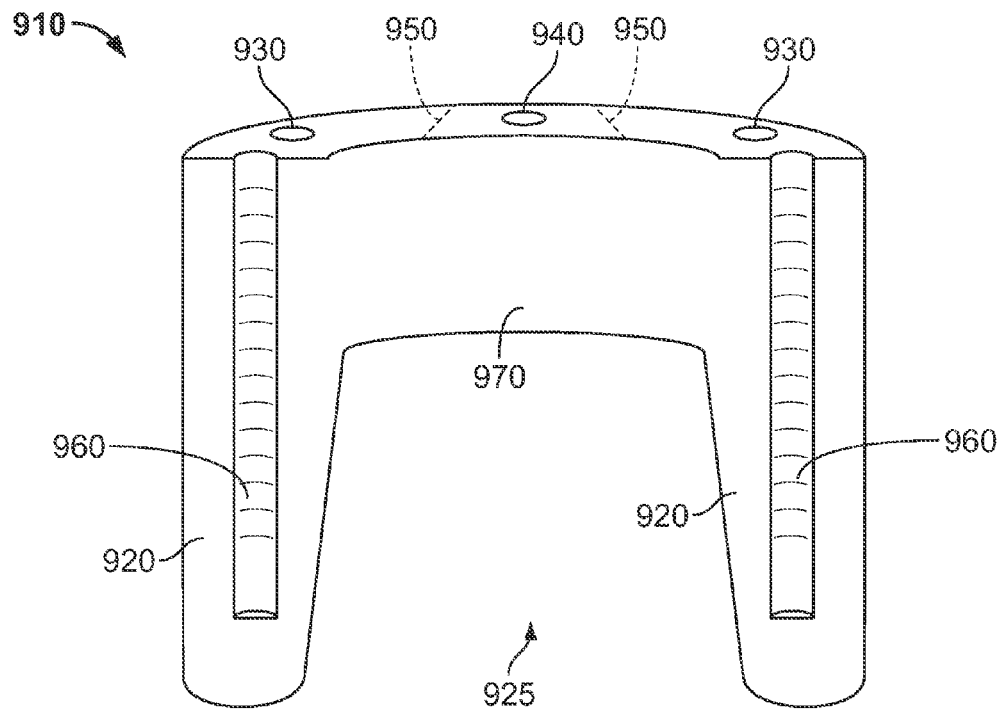
FIGS. 1 and 2 show a front perspective view and a back view, respectively, of an illustrative augment.
Figure 2:
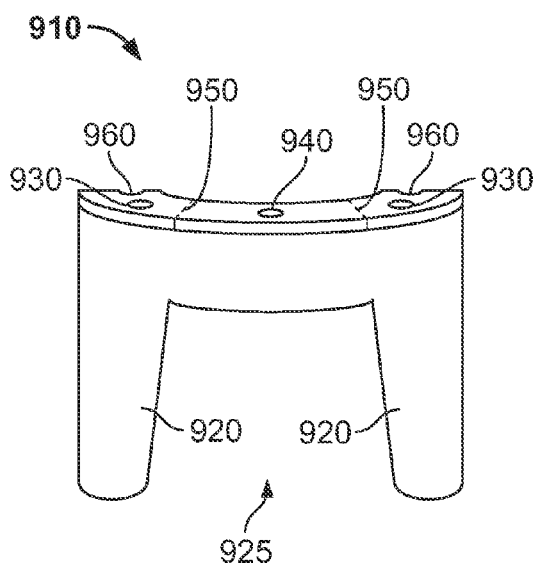

FIGS. 1 and 2 are a front perspective view and a back view, respectively, of an augment according to certain embodiments. In FIGS. 1 and 2, augment 910 is in the shape of a staple and is provided with a number of projections and optional fixation elements. For example, augment 910 includes two projections 920 extending from a base portion or member 970, although it is possible that the augment 910 may have three or more projections that extend from a base member as described below. As shown, the projections 920 may be disposed in substantially the same direction from the augment 910 defined by the respective axis of each projection, with a gap 925 between the two projections 920. In certain embodiments the projections 920 may be angled or otherwise offset such that the projections 920 are not disposed in the same direction from the augment 910; however, there may still preferably be a gap disposed between the two projections 920. Furthermore, although the length of the projections 920 is shown as being substantially the same, it will be understood that the length of one of the projections 920 may be different than the respective length of the other projection. The base member 970, or the projections 920, or both, may have a surface that is substantially arcuate, for example, in order to complement an outer curved surface of an acetabular shell or other implant.

Optional fixation elements include screw holes 930 and cement troughs 960. The fixation elements fix the augment 910 in place when implanted. Each fixation element may connect the augment 910 to a patient's bone, an acetabular shell, or both. The augment 910 may also include a connection element 940 on base member 970, for example, at the center top of the augment 910. In certain embodiments, connection element 940 is a threaded opening that may be attached to the end of a driver handle (e.g., driver handle 1060 of FIG. 7) for assisting with the implantation of the augment 910. However, the connection element 940 may be a tapered connection, a quick-connect, or any other type of fitting. The augment 910 may further include timing marks 950 to allow the augment 910 to be properly placed within the hip bone. Installation of the augment 910 is described in further detail below.

Figure 3:
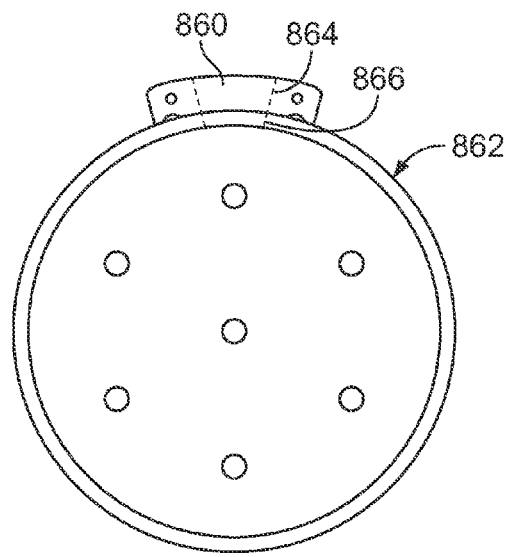
FIG. 3 shows a top plan view of an augment illustratively installed on an acetabular shell.

FIG. 3 is a top view of an augment installed on an acetabular shell. Augment 860 may be similar to augment 910. As shown, augment 860 is positioned next to acetabular shell 862 such that timing marks 864 disposed on the augment 860 are aligned with timing marks 866 disposed on the acetabular shell 862. The base member of augment 860 has an arcuate surface that contacts the complementary curved outer surface of the acetabular shell 862. As described above, an augment such as augment 860 may be fixed to the acetabular shell 862, a patient's bone, or both, via optional fixation elements such as screw holes and cement troughs.

FIGS. 4-7 illustrate exemplary methods for installing an augment 910 into a patient's joint according to certain embodiments.

Figure 4:
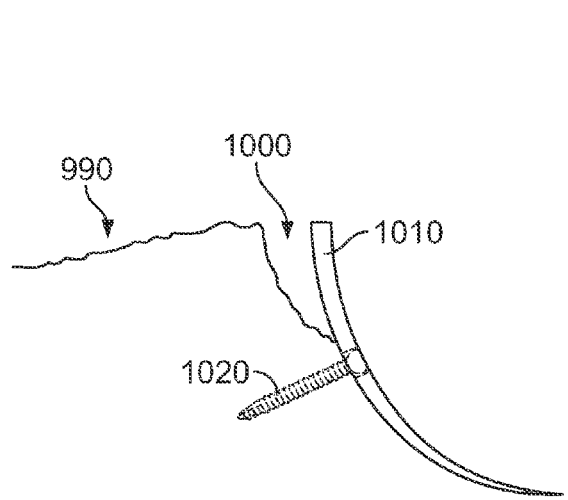
FIGS. 4-7 illustrate exemplary methods for installing an augment into a patient's joint.

FIG. 4 is a cross-sectional elevation drawing of an acetabulum 990 and an acetabular shell 1010. The acetabulum 990 would have been prepared to receive the shell 1010 by reaming, rasping or the like. Bone screws 1020 or other appropriate fixation devices have also been installed to secure shell 1010. Also shown is bone deficient area 1000. This area 1000 is avoid space extending from the outer wall of the acetabular shell 1010 to the acetabulum 990.

Figure 5:
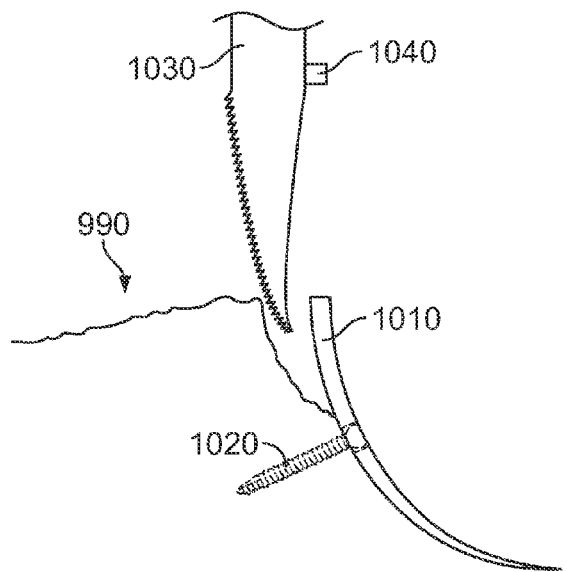

In FIG. 5, the acetabulum 990 is prepared for the augment 910 by use of broach 1030. The broach 1030 can be of any kind useful for rasping or reaming bone. For use with the augments described herein, the broach 1030 is typically provided with a depth stop 1040. Depth stop 1040 prevents the broach 1030 from removing too much bone by catching, for example, on the rim of acetabular shell 1010. The broach 1030 may have roughly the same cross-sectional profile and overall shape as the augment 910 and is typically sized to allow the augment 910 to be wedge-fitted into bone deficient area 1000. The broach 1030 may also have a slot provided therein to allow the broach 1030 to slide on either side of the installed screw 1020 to clear away bone on both sides of the screw 1020.

Figure 6:
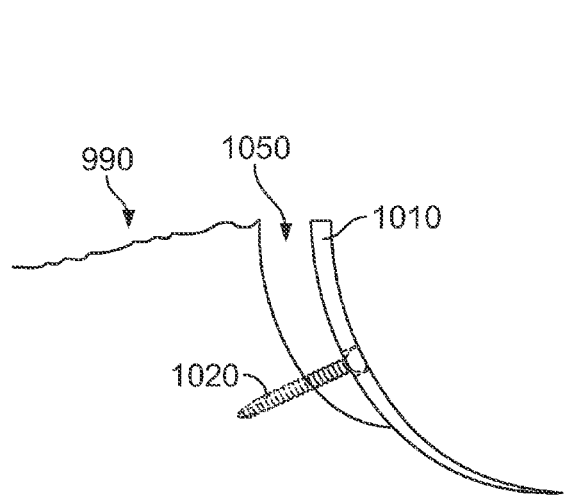

In FIG. 6, the acetabulum 990 has been prepared for the augment 910. Bone deficient area 1000 has been replaced with prepared space 1050 between the acetabulum 990 and the acetabular shell 1010, the prepared space including screw 1020.

Figure 7:
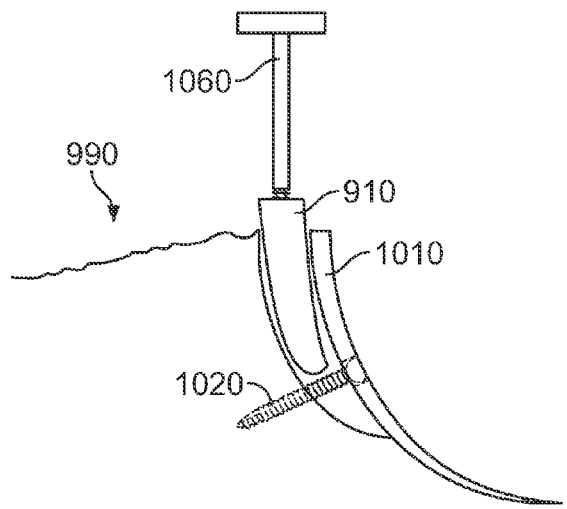

The next step in the procedure is illustrated in FIG. 7. The augment 910 is attached to driver handle 1060 and inserted into prepared space 1050. During insertion, the surgeon matches the timing marks 950 on the top of the augment 910 to timing marks (e.g., timing marks 886) on the acetabular shell 1010 to ensure that bone screw 1020 is avoided. The augment 910 is inserted into the prepared space by positioning the augment around the screw 1020 (or any other fixation member) such that the screw 1020 extends through the gap 925 between projections 920 of augment 910. Once the augment 910 has been pushed into place by hand, it may be tapped into its final position with a hammer. If the surgeon desires, the surgeon may then fix the augment 910 even further by using augment screws placed into screw holes 930 and then into the patient's bone. Alternatively or additionally, the surgeon can pour bone cement down the troughs 960 illustrated in FIG. 1. The cement may bind the augment 910 to the acetabular shell 1010, the patient's bone, or both.

In some embodiments, the augment 910 is held in place solely by a friction fit. In some embodiments, fixation devices like bone screws or cement may be used to secure augment 910 in place, for example, via screw holes 930 or cement troughs 960, respectively. Any kind of bone screw or cement familiar to one of ordinary skill in the art may be used.

FIG. 8 shows a front perspective view of an augment having three projections extending from a top or base member according to certain embodiments. For example, augment 910' may be similar to augment 910 of FIG. 1, but augment 910' includes three projections 920' extending from the top member 970'. It will be understood that in certain embodiments an augment may include more than three projections.

In some embodiments, the augments described above may be provided with flanges, blades, plates, hooks, any other suitable mounting members, or any combinations thereof. For example, FIG. 9 shows atop plan view of an augment 1080 with flange 1090. Flange 1090 may provide additional support for the augment 1080 on the outside of the acetabulum (e.g., acetabulum 1092 of FIG. 10). FIG. 10 illustrates a partial cross-section elevation view of an augment 1080 installed in acetabutum 1092 with flange 1090 having bone screw 1094 provided therethrough.

The augments described herein may be made of a number of materials, including Titanium, Cobalt-Chromium, Zirconium oxide, any other biocompatible materials or alloys that have the appropriate strength, resistance to wear, etc., or any combinations thereof. The augments may also be made fully porous or partially porous to allow for greater bone ingrowth, for example, and the augments may be coated with hydroxyapatite or any other bone-promoting agents or combinations thereof.

The embodiments described preferably above allow a surgeon to implant the acetabular shell or cup first and gain desired screw fixation and then prepare the bone minimally to fit a desired augment. This enables the surgeon to get the desired fixation for the acetabutar shell without compromising the surgeon's ability to use an augment. An additional advantage is that the surgeon removes no more bone than is necessary.

The foregoing is merely illustrative of the principles of the disclosure, and the systems, devices, and methods can be practiced by other than the described embodiments, which are presented for purposes of illustration and not of limitation. It is to be understood that the systems, devices, and methods disclosed herein, while shown for use in acetabular systems, may be applied to medical devices to be used in other surgical procedures including, but not limited to, spine arthroplasty, cranio-maxillofacial surgical procedures, knee arthroplasty, shoulder arthroplasty, as well as foot, ankle, hand, and extremities procedures.

Variations and modifications will occur to those of skill in the art after reviewing this disclosure. The disclosed features may be implemented, in any combination and subcombinations (including multiple dependent combinations and subcombinations), with one or more other features described herein. The various features described or illustrated above, including any components thereof, may be combined or integrated in other systems. Moreover, certain features may be omitted or not implemented.

Examples of changes, substitutions, and alterations are ascertainable by one skilled in the art and could be made without departing from the scope of the information disclosed herein. All references cited herein are incorporated by reference in their entirety and made part of this application.

What is claimed is:

1. A method of implanting an orthopedic device in a patient's acetabulum, the method comprising:
    preparing the patient's acetabulum to receive an acetabular shell;
    securing the acetabular shell using at least one bone screw;
    preparing a space in the patient's acetabulum by use of a broach;
    inserting an augment into the prepared space, the augment comprising at least two projections defining a gap therebetween, one or more of the at least two projections comprising a cement trough, wherein the augment is inserted into the prepared space by positioning the augment around the at least one bone screw such that the bone screw extends through the gap; and
    after inserting the augment into the prepared space, securing the augment by pouring cement into the cement trough.

2. The method of claim 1, further comprising fixing the augment further using an augment screw.

3. The method of claim 1, further comprising attaching the augment to a driver handle.

4. The method of claim 1, further comprising while inserting the augment, aligning the augment relative to the acetabular shell to facilitate positioning of the bone screw in the gap between the projections.

5. The method of claim 1, wherein the preparing the space in the patient's acetabulum comprises rasping or reaming the patient's acetabulum with the broach.

6. The method of claim 1, further comprising limiting an amount of bone removed from the patient's acetabulum by using a depth stop disposed on the broach.

7. The method of claim 1, wherein a cross-sectional profile of the broach is approximately the same as a cross-sectional profile of the augment.

8. The method of claim 1, wherein the augment further comprises flanges, blades, plates, or hooks attached thereto.

9. A method of implanting an orthopedic device in a patient's acetabulum, the method comprising:
    preparing the patient's acetabulum to receive an acetabular shell;
    securing the acetabular shell using at least one bone screw;
    preparing a space in the patient's acetabulum by use of a broach;
    inserting an augment into the prepared space, the augment comprising at least two projections defining a gap therebetween, one or more of the at least two projections comprising a cement trough, wherein the augment is inserted into the prepared space by positioning the augment around the at least one bone screw such that the bone screw extends through the gap;
    while inserting the augment, matching timing marks on the augment to timing marks of the acetabular shell; and
    after inserting the augment into the prepared space, securing the augment by pouring cement into the cement trough.

10. The method of claim 9, further comprising setting the augment using screws.

11. The method of claim 9, wherein the inserting the augment into the prepared space comprises attaching the augment to a driver handle for positioning the augment into the prepared space.

12. The method of claim 9, further comprising aligning the augment relative to the acetabular shell using the timing markings to facilitate positioning of the bone screw in the gap between the projections during the inserting of the augment into the prepared space.

13. The method of claim 9, wherein the preparing the space in the patient's acetabulum comprises rasping or reaming the patient's acetabulum with the broach, and wherein a cross-sectional profile of the broach is approximately the same as a cross-sectional profile of the augment.

* * * * *